(12) United States Patent
Grosjacques et al.

(10) Patent No.: US 10,624,825 B2
(45) Date of Patent: Apr. 21, 2020

(54) METHOD FOR HOMOGENOUSLY DYEING KERATINOUS FIBERS

(71) Applicant: Henkel AG & Co. KGaA, Duesseldorf (DE)

(72) Inventors: Camille Grosjacques, Hamburg (DE); Susanne Hagenow, Hamburg (DE); Sylvia Kerl, Boenningstedt (DE); Hartmut Manneck, Barnitz (DE); Astrid Kleen-Fehres, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/220,972

(22) Filed: Dec. 14, 2018

(65) Prior Publication Data

US 2019/0183763 A1    Jun. 20, 2019

(30) Foreign Application Priority Data

Dec. 19, 2017    (DE) .................. 10 2017 223 245

(51) Int. Cl.

| | |
|---|---|
| *A61Q 5/10* | (2006.01) |
| *A61K 8/41* | (2006.01) |
| *A61K 8/49* | (2006.01) |
| *A61K 8/46* | (2006.01) |
| *A61K 8/22* | (2006.01) |
| *A61K 8/362* | (2006.01) |
| *A61K 8/20* | (2006.01) |
| *A61K 8/23* | (2006.01) |
| *A61K 8/24* | (2006.01) |
| *A61K 8/365* | (2006.01) |

(52) U.S. Cl.
CPC .............. *A61K 8/411* (2013.01); *A61K 8/20* (2013.01); *A61K 8/22* (2013.01); *A61K 8/23* (2013.01); *A61K 8/24* (2013.01); *A61K 8/362* (2013.01); *A61K 8/365* (2013.01); *A61K 8/415* (2013.01); *A61K 8/463* (2013.01); *A61K 8/4953* (2013.01); *A61K 2800/4324* (2013.01); *A61K 2800/5426* (2013.01); *A61K 2800/884* (2013.01)

(58) Field of Classification Search
CPC ........ A61Q 5/10; A61K 8/411; A61K 8/4926; A61K 8/415; A61K 8/22; A61K 8/347; A61K 2800/4324; A61K 2800/882; A61K 2800/884; A61K 31/05
See application file for complete search history.

(56) References Cited

U.S. PATENT DOCUMENTS 8,394,151 B2 *   3/2013   Fujinuma ............... A61K 8/046
                                                              132/202

FOREIGN PATENT DOCUMENTS

| EP | 1479371 A1 | 11/2004 | |
|---|---|---|---|
| EP | 2272496 A1 | 1/2011 | |
| EP | 2471504 A1 | 7/2012 | |
| EP | 2881143 A2 | 6/2015 | |
| EP | 2881145 A2 | 6/2015 | |
| EP | 2881146 A2 * | 6/2015 | ............... A61Q 5/10 |
| WO | 9301792 A | 2/1993 | |
| WO | 2013126657 A2 | 8/2013 | |
| WO | 2015026991 A2 | 2/2015 | |
| WO | 2015026992 A2 | 2/2015 | |
| WO | 2015026994 A1 | 2/2015 | |

* cited by examiner

*Primary Examiner* — Eisa B Elhilo
(74) *Attorney, Agent, or Firm* — Lorenz & Kopf, LLP

(57) ABSTRACT

The object of the present disclosure is a method for dyeing human hair which is adapted to the differing degrees of damage along the length of the hair fiber and achieves more homogenous coloring results.

19 Claims, No Drawings

METHOD FOR HOMOGENOUSLY DYEING KERATINOUS FIBERS

CROSS-REFERENCE TO RELATED APPLICATION

This application claims priority to Germam Patent Application No. 10 2017 223 245.5, filed Dec. 19, 2017, which is incorporated herein by reference in its entirety.

TECHNICAL FIELD

The present disclosure is directed to the field of cosmetics and relates to methods for oxidative dyeing of hair, wherein application mixtures are used that are prepared in a special mixing process.

BACKGROUND

Changing the color of keratinous fibers, particularly hair, represents an important aspect of modern cosmetics. It serves as a way to adapt the appearance of the hair either in keeping with current fashion trends or to reflect the personal wishes of the individual. The person skilled in the art is familiar with various options for changing hair color. Hair color can be changed temporarily through the use of direct coloring agents. In this process, ready-to-use coloring agents are diffused from the dyes into the hair fiber. Coloring with direct coloring agents is associated with minor hair damage, but one disadvantage is that coloring obtained with direct coloring agents offers low hold stability and is soon washed out of the hair.

If the consumer wishes to obtain a long-lasting coloring result or a tint which is lighter than his or her original hair color, typically oxidative color changing agents are used. For permanent, intensive coloring with corresponding authenticity properties, "oxidation dyes" are used. Such dyes usually contain oxidation dye precursors, substances called developer components, and coupling components, which combine to constitute the actual coloring agents under the effects of the oxidizing agents. Oxidation dyes are notable for their long-lasting dyeing results.

In the hairdressing salon setting, the level 3 colorations are used particularly often. Level 3 colorations are oxidative dyes with particularly good stability and very effective gray coverage capability.

This good stability and good gray coverage can be achieved due to a high ammonia content in the colorations, which causes the hair to swell significantly and consequently allows the oxidation dye precursors to diffuse into the hair at a high rate. In the case of dark tints of the level 3 colorations, the content of oxidation dye precursors is also relatively high. But this high ammonia content is also associated with substantial hair damage.

At home, those who prefer not to expose their hair to such substantial damage every time they dye it can decide to use level 2 products instead. The level 2 products are also oxidative dyes, but they contain less ammonia, or alternative alkalizing agents which do not cause the hair to swell as much are used instead of ammonia. In the home user market, level 3 and level 2 products are packaged separately and are marketed as distinct products, so the user can choose and apply either a level 3 product or a level 2 product.

In the hairdressing salon, the hairdresser offers the customer a much more extensive spectrum of shading options. Thus, a complete range of level 3 dyes includes an extremely varied palette coloring creams, each of which is mixed with the usual composition of level 3 oxidizing agents shortly before use. For reasons of capacity and storage, the hairdresser will avoid keeping a complete range of both level 3 and level 2 shading products.

BRIEF SUMMARY

Methods for dyeing human hair are provided herein. In an exemplary embodiment, a method includes mixing a first portion of a first component (K1) with a second component (K2) to obtain a first mixture (M1). The first mixture (M1) is applied to selected regions of the hair including a hair anchor point. A second portion of the first component (K1) is mixed with a third component (K3) to obtain a second mixture (M2). The second mixture (M2) is applied to selected regions of the hair, which were not treated with the first mixture (M1), including to a hair shaft and/or hair tips. The first and second mixtures (M1) and (M2) are allowed to take effect on the hair for a period from about 30 seconds to about 60 minutes at about room temperature and/or at from about 30 to about 60° C. The first and second mixtures (M1) and (M2) are rinsed out of the hair. The first component (K1) is an aqueous dye preparation which comprises at least one oxidation dye precursor and has a pH value from about 8 to about 11, measured at 22° C. The second component (K2) is an aqueous hydrogen peroxide preparation which comprises no oxidation dye precursors and has a pH value from about 3 to about 6.9, measured at 22° C. The third component (K3) is an aqueous hydrogen peroxide preparation which comprises no oxidation dye precursors and has a pH value from about 1.0 to about 2.8, measured at 22° C. The pH value of the first mixture (M1) is at least about 0.2 units lower than the pH value of the component (K1). The pH value of the second mixture (M2) is at least about 0.2 units lower than the pH value of the first component (M1).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was therefore a first object of the present disclosure to provide the hairdresser with a flexible, easily usable method that allows the hairdresser to create a level 2 produce from a level 3 product.

Additionally, the degree of damage to the hair varies from the anchor point to the tip. Hair close to the anchor point has just been recently washed and has as yet been exposed to little or no weather effects or chemical (dyeing, lightening, perm, washing, swimming pool water) or physical (combing, hairdryer) influences. Damage to the hair increases over the shaft of the hair with increasing distance from the anchor point, as the hair is older there. The area close to the tips includes the oldest parts of the hair and therefore have the greatest damage.

In damaged hair, the cuticle—the scaly layer covering the hair shaft—is destroyed to a greater or lesser degree. Consequently, the dye is generally taken up more strongly by damaged hair. Consequently, if the anchor point and the tips are colored with the same dye, there is always the risk of an uneven dyeing result with more heavily damaged hair.

For the purposes of the present application, the tips of the hair are considered to be part of the hair shaft. References to the hair shaft thus always imply the tips of the hair as well.

The hair anchor point as contemplated herein is understood to be the portion of the hair which is closest to the scalp (the first 0 to 5 cm of the hair).

Accordingly, the area of the hair shaft is understood to refer to the area of the hair fiber that is more than about 5 cm distant from the scalp. As contemplated herein the area of the hair tips is understood to include the last about 3 cm of the hair fiber.

It was a further object of the present disclosure to provide the hairdresser or the home user with a system in which he/should can reduce the concentration of coloring agent in the hair dye easily, specifically and reproducibly depending on his/her assessment of the degree of damage sustained by the hair which is to be dyed.

In principle, both the preparation of a level 2 dyeing product from a level 3 product and the reduction of coloring agent concentration for use on certain portions of the hair may be achieved by diluting the oxidative level 3 product. Various options for this are already known in the related art. EP 2881145A2, EP 2881146A2 and WO2013126657A2 disclose oxidative hair dyeing methods in which first an oxidizing agent composition and a coloring cream containing an alkalizing agent are mixed with each other, and a portion of this mixture is applied without further dilution to the hair, preferably to the hair anchor point, while the remaining part of the mixture is an aqueous and/or a non-aqueous solution and then also applied to the hair, particularly to the hair shaft. The person skilled in the art also knows further ways to improve the homogeneity of a dyeing result and/or reduce the selectivity of a dye and/or improve the balancing capability of a dye. EP 2471504A1 deals with the problem of providing oxidative hair coloring products with high balancing capability, that is to say they produce uniform hair coloring on both the damaged parts of the hair fiber and on the undamaged or only mildly damaged hair anchor point. EP 2471504A1 solves this problem with a combination of active agents including an amino acid-based tenside, a cationic tenside and an oil. The oxidizing agent compositions used for exemplary purposes have a relatively low pH value of 2.5 or 3, which has been adjusted in each case with phosphoric acid. A single mixture was produced from the respective oxidizing agent composition and the coloring agent cream, and this was applied to all of the hair.

One option for diluting is for example to mix the application-ready oxidative dye with a conditioner. Since conditioners are often adjusted to a mildly acidic pH value, this can be used to lower the pH value of the dye and so reduce the degree to which the hair is swollen. However, due to the presence of the care substances (certain polymers, silicones, ionic tensides etc.) contained in the conditioner, dilution with the conditioner can lead to a color shift, so that the resulting color no longer matches the desired shade.

A further option for diluting consists in mixing the application-ready oxidative dye with a shampoo. Since shampoos contain relatively quantities of detergent surfactants, the foam formation during use may be so abundant that it is no longer possible to guarantee that all of the hair will be wetted with the diluted dye. Moreover, if the shampoo is not sufficiently acidic excessive quantities of the shampoo will be needed to dilute the dye. Surprisingly, it has now been found that the dye can be diluted flexibly, quickly and conveniently without the disadvantages described previously if the hairdresser implements a method in which first a coloring lotion (K1) containing an alkalizing agent is mixed with a first oxidizing agent composition (K2), and a first homogenous mixture (M1) is prepared from these two components and then applied the hair, preferably to the hair anchor point, then a further portion of the same coloring lotion (K1) containing an alkalizing agent is mixed with a second oxidizing agent composition (K3), and a second homogenous mixture (M2) is prepared from these two components and then applied to the hair that was not treated with (M1), preferably particularly to the hair shaft/hair tips, wherein the second oxidizing agent composition (K3) has a considerably lower pH value than the first oxidizing agent composition (K2). After the exposure time, both hair dyes are rinsed out of the hair and the hair is given follow-up treatment as usual, e.g., with a shampoo and/or conditioner with final drying of the hair. The second oxidizing agent composition (K3) is balanced with the coloring lotion (K1) so that homogenous coloring is achieved over the length of the hair fiber regardless of the overall degree of damage to the hair. Also preferably, the three components (K1), (K2) and (K3) are balanced with each other in such manner that mixing ratio (K1):(K2) indicated for a certain shade for the hair anchor may also be used for the mixing ratio (K1):(K3) for the hair shaft and the hair tips.

Thus, the hairdresser only needs to keep one line of coloring lotions (K1) in stock; he/she then combines the coloring lotion (K1) either with the less acidic oxidizing agent composition (K2) or with the more acidic oxidizing agent composition (K3) depending on the degree of level 3 coloring or level 2 coloring needed. In such context, the mixture (M2) has a lower pH value than the mixture (M1) and thus creates less drastic reaction conditions on previously damaged hair. Also preferably, the three components (K1), (K2) and (K3) are balanced with each other in such manner that the mixture (M1) produces the same shade of hair coloring in areas of the hair fiber (hair anchor point) that have undergone little or no prior damage as the mixture (M2) produces on the portions of the hair fiber (hair shaft/hair tips) which are damaged.

A first object of the present disclosure is a method for dyeing human hair comprising the following steps in the sequence indicated:

A) Mixing a first portion of a first component (K1) with a second component (K2) to obtain a first mixture (M1),
B) Applying the mixture (M1) to selected regions of the hair, particularly the hair anchor point,
C) Mixing a second portion of the first component (K1) with a third component (K3) to obtain a second mixture (M2),
D) Applying the mixture (M2) to selected regions of the hair which were not treated with (M1), particularly the hair shaft/hair tips,
E) Allowing the mixtures (M1) and (M2) to take effect on the hair for a period from about 30 seconds to about 60 minutes, preferably from about 20 to about 45 minutes at about room temperature and/or at about 30 to about 60° C., preferably at about 32 to about 50° C.,
F) Rinsing the mixtures (M1) and (M2) out of the hair, wherein the component (K1) is an aqueous dye preparation which contains at least one oxidation dye precursor and has a pH value in the range from about 8 to about 11, preferably in the range from about 8.5 to about 10.7, particularly preferably in the range from about 9 to about 10.1, measured in each case at 22° C., the second component (K2) is an aqueous hydrogen peroxide preparation which contains no oxidation dye precursors and has a pH value in the range from about 3 to about 6.9, preferably from about 3.1 to about 4.5, particularly preferably from about 3.2 to about 4.0, measured in each case at 22° C., and the third component (K3) is an aqueous hydrogen peroxide preparation which contains no oxidation dye precursors and has a pH value in the range from about 1.0 to about 2.8, preferably from about 1.2 to about 2.4, particularly preferably from about 1.4 to about 2.0, measured in each case at 22° C., and the pH value of the mixture (M1) is at least about 0.2 units lower than the pH value of the component (K1) and the pH value of the mixture (M2) is at least about 0.2 units lower than the pH value of the component (M1).

As contemplated herein, the term "room temperature" denotes the temperature in the room in which a person usually uses a hair dye, that is to say typically a bathroom or a hairdresser's salon, in which a temperature in the range from about 10-about 29° C. normally prevails.

The hair coloring application mixtures (M1) and (M2) in method step D) of the hair coloring methods as contemplated herein or the preferred inventive hair coloring methods may also be allowed to work at temperatures of at least 30° C., preferably from about 30-about 60° C., particularly preferably from about 32-about 50° C. if the hair is warmed for example with a warming hood or radiant warmer.

The components (K1) (K2) and (K3) are cosmetic products which contain all essential ingredients, each in an aqueous cosmetic medium.

In a first step A), a first portion of a first component (K1) is mixed with a second component (K2). The first component (K1) is an aqueous dye preparation which contains at least one oxidation dye precursor and has a pH value in the range from about 8 to about 11, preferably in the range from about 8.5 to about 10.7, particularly preferably in the range from about 9 to about 10.1, measured in each case at 22° C.

The first component (K1) preferably contains at least one oxidation dye precursor of the developer type and at least one oxidation dye precursor of the coupling type.

The first component (K1) preferably contains at least one oxidation dye precursor selected from the group including p-toluylene diamine, 2-(2-hydroxyethyl)-p-phenylene diamine, N,N-bis-(2-hydroxyethyl)-p-phenylene diamine, 2-methoxymethyl-p-phenylene diamine, N-(4-amino-3-methylphenyl)-N-[3-(1H-imidazole-1-yl)propyl]amine, bis-(2-hydroxy-5-aminophenyl)methane, 4-aminophenol, 4-amino-3-methylphenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine and/or physiologically tolerable salts thereof.

The second component (K2) is an aqueous hydrogen peroxide preparation which contains no oxidation dye precursors and has a pH value in the range from about 3 to about 6.9, preferably from about 3.1 to about 4.5, particularly preferably from about 3.2 to about 4.0, measured in each case at 22° C.

Die first component (K1) and the second Component (K2) may be mixed together by stirring or shaking, for example, to create the first mixture (M1).

The pH value of the mixture (M1) is at least 0.2 units lower than the pH value of component (K1).

In a preferred embodiment of the method as contemplated herein, the first component (K1) and the second Component (K2) are mixed with each other in a weight ratio from about 3:1 to about 1:3, preferably from about 2:1 to about 2:1, most particularly preferably about 1:1.

In the second step, the mixture (M1) as contemplated herein is applied to selected regions of the hair, particularly the hair anchor point.

In the third step, a second portion of the first component (K1) is mixed with a third component (K3) to obtain a second mixture (M2).

The third component (K3) is an aqueous hydrogen peroxide preparation which contains no oxidation dye precursors and has a pH value in the range from about 1.0 to about 2.8, preferably from about 1.2 to about 2.4, particularly preferably from about 1.4 to about 2.0, measured in each case at 22° C.

The pH value may be measured for example with a glass electrode which is usually in the form of a single rod combined electrode. The pH values of the present disclosure are pH values which have been measured at a temperature of 22° C.

The first component (K1) and the third component (K3) may also be mixed together by stirring or shaking, for example, to produce the second mixture (M2).

It is essential for the purposes of the disclosure that the pH value of mixture (M2) is at least about 0.2 units lower than the pH value of mixture (M1).

In a preferred embodiment of the method as contemplated herein, first component (K1) and the third component (K3) are mixed together in a weight ratio from about 3:1 to about 1:3, preferably from about 2:1 to about 2:1, most particularly preferably about 1:1. The mixing ratio (K1):(K2) and (K1):(K3) are freely selectable, independently of each other. However, it may be preferable as contemplated herein if the weight ratio (K1):(K2) is identical to the weight ratio (K1):(K3) within the same method. This makes the hairdresser's work easier, since he/she then only has to note one mixing ratio for preparing both mixtures (M1) and (M2).

In the fourth step, the mixture (M2) as contemplated herein is applied to regions of the hair that have not been treated with (M1), particularly the hair shaft and/or the hair tips.

After the application, in step E) the mixtures (M1) and (M2) are then allowed to take effect on the hair for a period of from about 30 seconds to about 60 minutes, preferably from about 20 to about 45 minutes, at room temperature and/or at about 30 to about 60° C., preferably at about 32 to about 50° C. In this context, it is possible and falls within the scope of the disclosure to leave the mixture (M2) on all regions of the hair that have been treated with (M2) for a certain period. In a further embodiment, however, it is also possible to choose different exposure periods for different regions of the hair, so that for example the exposure period in the region of the hair shaft, particularly the upper part of the hair shaft close to the anchor point is longer than the exposure period close to the damaged tips.

After they have been allowed to take effect for the exposure time, in step F) the mixtures (M1) and (M2) are then rinsed out of the hair again. Rinsing may be done either with water alone or with the aid of a shampoo.

Steps A) to F) are the steps of a single dyeing process, i.e. all steps are carried out as contemplated herein during a single dyeing process, i.e. within a period of not more than about 6 hours, preferably within a period of not more than about 3 hours.

In the method as contemplated herein, the sequence of the steps is also fixed, and it takas place in the order A), followed by B), followed by C), followed by D) followed by E) followed by F).

In order to guarantee that the consistency of mixture (M1) is suitable for the application, a method for dyeing human hair that is preferred as contemplated herein is exemplified in that the second component (K2) contains one or more lipids in a total quantity from about 0.1 to about 70% w/w, preferably from about 2 to about 50% w/w, more preferably from about 3.5 to about 21% w/w and most particularly preferably from about 8 to about 15% w/w relative to the weight thereof in each case.

In order to guarantee that the consistency of mixture (M2) is suitable for the application, a method for dyeing human hair that is preferred as contemplated herein is exemplified in that the third component (K3) contains one or more lipids in a total quantity from about 0.1 to about 70% w/w, preferably from about 2 to about 50% w/w, more preferably from about 3.5 to about 21% w/w and most particularly preferably from about 8 to about 15% w/w relative to the weight thereof in each case.

For the purposes of the disclosure, "lipids" are understood to be organic compounds with a solubility in water less than 1% w/w, preferably less than 0.1% w/w at room temperature (22° C.) and under pressure of 1013 mbar. The definition of lipids explicitly includes only uncharged (i.e., nonionic) compounds. Lipids include at least one saturated or unsaturated alkyl group with at least 8 C atoms. The lipids have a molar mass not exceeding about 5000 g/mol, preferably not exceeding 2500 g/mol and particularly preferably not exceeding about 1000 g/mol. The lipids are neither polyoxyalkylated nor polyglycerylized compounds.

Preferred lipids in this context are the components from the group of C12-C30 fatty alcohols, C12-C30 fatty acid triglycerides, esters of linear or branched saturated or unsaturated fatty alcohols with from about 2-about 30 carbon atoms with linear or branched saturated or unsaturated fatty acids with from about 2-about 30 carbon atoms, which may be hydroxylated, C12-C30 fatty acid monoglycerides, C12-C30 fatty acid diglycerides and/or hydrocarbons. For the purposes of the present disclosure, explicitly only non-ionic substances are considered as lipids. Charged compounds such as fatty acids and their salts are not considered as lipids.

The C12-C30 fatty alcohols may be saturated, mono- or polyunsaturated, linear or branched fatty alcohols with from about 12 to about 30 C atoms. Examples of preferred linear, saturated C12-C30 fatty alcohols are 1-dodecanol (dodecyl alcohol, lauryl alcohol), 1-tetradecanol (tetradecyl alcohol, myristyl alcohol), 1-hexadecanol (hexadecyl alcohol, cetyl alcohol), 1-octadecanol (octadecyl alcohol, stearyl alcohol), arachyl alcohol (1-eicosanol), heneicosyl alcohol (1-heneicosanol) and/or behenyl alcohol (1-docosanol).

Preferred linear, unsaturated fatty alcohols are Z-9-octadecen-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidonic alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol). The preferred representatives of the branched fatty alcohols are 2-octyldodecanol, 2-hexyldodecanol and/or 2-butyldodecanol.

For the purposes of the present disclosure, the triester of the trivalent alcohol glycerol with three fatty acid equivalents is understood to be a C12-C30 fatty acid triglyceride. In such case, fatty acids with both identical and different structures may also be involved in ester formations within a triglyceride molecule.

As contemplated herein, fatty acids that are to be considered suitable for forming the aforementioned C12-C30 fatty acid triglycerides are saturated or unsaturated, unbranched or branched, unsubstituted or substituted C12-C30 carboxylic acids. Unsaturated fatty acids may be mono- or polyunsaturated. In the case of an unsaturated fatty acid, the C—C double bond(s) thereof may have a cis- or trans-configuration.

Particularly preferred fatty acid triglycerides as contemplated herein are those in which at least one of the ester groups is formed on a glycerol base with a fatty acid that is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-Octadecenoic acid], palmitoleic acid [(9Z)-Hexadec-9-enoic acid], oleic acid [(9Z)-Octadec-9-enoic acid], elaidic acid [(9E)-Octadec-9-enoic acid], erucic acid [(13Z)-Docos-13-enoic acid], linoleic acid [(9Z,12Z)-Octadeca-9,12-dienoic acid, linolenic acid [(9Z,12Z,15Z)-Octadeca-9,12,15-trienoic acid, eleostearic acid [(9Z,11E,13E)-Octadeca-9,11,3-trienoic acid], arachidonic acid [(5Z,8Z,11Z,14Z)-Icosa-5,8,11,14-tetraenedoic acid] and/or nervonic acid [(15Z)-Tetracos-15-enoic acid].

The fatty acid triglycerides may also be of natural origin. The fatty acid triglycerides and/or mixtures thereof which occur in soybean oil, peanut oil, olive oil, sunflower oil, macadamia nut oil, moringa oil, apricot kernel oil, marula oil and/or optionally hydrogenated castor oil are particularly suitable for use in the method as contemplated herein.

Further lipids that are particularly preferred as contemplated herein are selected from the esters of linear or branched saturated or unsaturated fatty alcohols having 2-30 carbon atoms with linear or branched saturated or unsaturated fatty acids having 2-30 carbon atoms, which may or may not be hydroxylated. These preferably include 2-Hexyldecyl stearate, 2-Hexyldecyl laurate, isodecyl neopentanoate, isononyl isononanoate, 2-Ethylhexyl palmitate and 2-Ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-Ethylhexyl laurate, 2-Ethylhexyl isostearate, 2-Ethylhexyl cocoate, 2-Octyldodecyl palmitate, butyloctanoic acid-2-butyl octanoate, diisotridecyl acetate, n-Butyl stearate, n-Hexyl laurate, n-Decyl oleate, oleyl oleate, oleyl erucate, erucyl oleate, erucyl erucate, ethyleneglycol dioleate and ethyleneglycol dipalmitate.

A C12-C30 fatty acid monoglyceride is understood to be the monoester of the trivalent alcohol glycerol with an equivalent fatty acid. In this context, either the middle hydroxy group of the glycerol or the terminal hydroxy group of the glycerol may be esterified with the fatty acid.

Particularly preferred C12-C30 fatty acid monoglycerides as contemplated herein are those in which a hydroxy group of the glycerol is esterified with a fatty acid, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachinic acid), docosanoic acid (behenic acid), petroselinic acid [(Z)-6-Octadecenoic acid], palmitoleic acid [(9Z)-Hexadec-9-enoic acid], oleic acid [(9Z)-Octadec-9-enoic acid], elaidic acid [(9E)-Octadec-9-enoic acid], erucic acid [(13Z)-Docos-13-enoic acid], linoleic acid [(9Z,12Z)-Octadeca-9,12-dienoic acid, linolenic acid [(9Z,12Z,15Z)-Octadeca-9,12,15-trienoic acid, eleostearic acid [(9Z,11E,13E)-Octadeca-9,11,3- trienoic acid], arachidonic acid [(5Z,8Z,11Z,14Z)-Icosa-5,8,11,14-tetraenedoic acid] or nervonic acid [(15Z)-Tetracos-15-enoic acid].

A C12-C30 fatty acid diglyceride is understood to be the diester of the trivalent alcohol glycerol with two equivalent fatty acids. In this context, either the middle and one terminal hydroxy group of the glycerol may be esterified with two equivalent fatty acids, or both terminal hydroxy groups of the glycerol may be esterified with one fatty acid each. In such case, the glycerol may be esterified with two structurally identical or two structurally different fatty acids.

Particularly preferred C12-C30 fatty acid diglycerides as contemplated herein are those in which at least one of the hydroxy groups is formed with a fatty acid based on glycerol which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachinic acid), docosanoic acid (behenic acid), petroselic acid [(Z)-6-Octadecenoic acid], palmitoleic acid [(9Z)-Hexadec-9-enoic acid], oleic acid [(9Z)-Octadec-9-enoic acid], elaidic acid [(9E)-Octadec-9-enoic acid], erucic acid [(13Z)-Docos-13-enoic acid], linoleic acid [(9Z,12Z)-Octadeca-9,12-dienoic acid], linolenic acid [(9Z,12Z,15Z)-Octadeca-9,12,15-trienoic acid, eleostearic acid [(9Z,11E,13E)-Octadeca-9,11,3-trienoic acid], arachidonic acid [(5Z,8Z,11Z,14Z)-Icosa-5,8,11,14-tetraenedoic acid] and/or nervonic acid [(15Z)-Tetracos-15-enoic acid].

Hydrocarbons are compounds which consist exclusively of carbon and hydrogen atoms with 8 to 80 C atoms. In this context, aliphatic hydrocarbons such as mineral oils, liquid paraffin oils (e.g., *Paraffinum liquidum* or *Paraffinum perliquidum*), isoparaffin oils, semi-solid paraffin oils, paraffin waxes, hard paraffin (*Paraffinum solidum*), vaseline, vaseline oil and polydecene are particularly preferred.

Suitable paraffin oils have proven to be in particular liquid paraffin oils (*Paraffinum liquidum* and *Paraffinum perliquidum*). Most particularly preferably, the hydrocarbon is *Paraffinum liquidum*, also called liquid paraffin. *Paraffinum liquidum* is a mixture of purified, saturated aliphatic hydrocarbons which consists mostly of hydrocarbon chains having a C chain distribution of 25 to 35 C atoms.

Preferred lipids are selected from the group of C12-C30 fatty alcohols, C12-C30 fatty acid triglycerides, esters of linear or branched saturated or unsaturated fatty alcohols with 2-30 carbon atoms having linear or branched saturated or unsaturated fatty acids with 2-30 carbon atoms, which may or may not be hydroxylated, C12-C30 fatty acid monoglycerides, C12-C30 fatty acid diglycerides and/or hydrocarbons. The C12-C30 fatty alcohols and/or the hydrocarbons are preferred lipids. Most particularly preferred lipids are the C12-C30 fatty alcohols.

The objective of mixing the coloring lotion (K1) with the oxidizing agent composition (K3) is a controlled reduction of the pH value of the application mixture (M2) which is to be applied to the hair shaft and hair tips, which exhibit a greater degree of damage than the hair at the hair anchor point. Associated with this is a reduction of the extent to which the hair swells when (M2) is used compared with the application of (M1). The mixture (M1), which is obtained by mixing (K1) and (K2), has a pH which is at least 0.2 units lower than the component (K1). Since oxidizing agent composition (K3) has a lower pH value than oxidizing agent composition (K2), the mixture (M2) which is obtained subsequently by mixing (K1) with (K3) has a pH value which is at least 0.2 units lower than the mixture (M1) obtained from (K1) and (K2), particularly when (K1) and (K2) are mixed with each other in the same weight ratio to each other as (K1) and (K3), as is particularly preferred as contemplated herein. In this way, the intention is to make it possible for the hairdresser to dye the customer's hair—which may have undergone significant damage following repeated dyeing treatments—with no shifting of the customary shade, but at the same time to avoid damaging the hair further as far as possible.

In order to adjust the pH value in the range from about 1.0 to about 2.8, preferably from about 1.2 to about 2.4, particularly preferably from about 1.4 to about 2.0, measured in each case at 22° C., component (K3) contains at least one acid.

A reduction of the pH value without a perceptible shift in color (between diluted and undiluted dye) is possible of the component (K3) contains at least one acid selected from the group including lactic acid, citric acid, malic acid, tartaric acid, maleic acid, succinic acid, oxalic acid, ascorbic acid, sulfuric acid, hydrochloric acid and/or phosphoric acid.

In a particularly preferred embodiment, the method for dyeing human hair is exemplified in that the third component (K3) contains at least one acid selected from the group including lactic acid, citric acid, malic acid, tartaric acid, maleic acid, succinic acid, oxalic acid, ascorbic acid, sulfuric acid, hydrochloric acid and/or phosphoric acid.

In this context, the addition of lactic acid, malic acid, tartaric acid or phosphoric acid to (K3) has been found to be most particularly suitable.

In a most particularly preferred embodiment, the method for dyeing human hair is exemplified in that the third component (K3) contains at least one acid selected from the group including lactic acid, malic acid, tartaric acid and phosphoric acid.

In order to be able to guarantee that the pH value is lowered effectively, the one or more acid(s) is/are contained in the component (K3) preferably in a total quantity from about 0.5 to about 15.0% w/w, preferably from about 1.0 to about 8.0% w/w, more preferably from about 1.5 to about 6.0% w/w and most particularly preferably from about 2.5 to about 5.5% w/w, relative in each case to the weight of component (K3).

In a particularly preferred embodiment, the method for dyeing human hair is exemplified in that the third component (K3) contains one or more acids in a total quantity from about 0.5 to about 15.0% w/w, preferably from about 1.0 to about 8.0% w/w, more preferably from about 1.5 to about 6.0% w/w and most particularly preferably from about 2.5 to about 5.5% w/w, relative to the weight thereof in each case.

In a particularly preferred embodiment, the method for dyeing human hair is exemplified in that the third component (K3) contains from about 2.5 to about 10.0% w/w lactic acid relative to its weight.

In a particularly preferred embodiment, the method for dyeing human hair is exemplified in that the third component (K3) contains from about 3.0 to about 8.0% w/w lactic acid relative to its weight.

In a particularly preferred embodiment, the method for dyeing human hair is exemplified in that the third component (K3) contains from about 3.5 to about 6.0% w/w lactic acid.

In a particularly preferred embodiment, the method for dyeing human hair is exemplified in that the third component (K3) contains from about 3.8 to about 5.5% w/w lactic acid.

In a particularly preferred embodiment, the method for dyeing human hair is exemplified in that the third component (K3) contains from about 0.5 to about 15.0% w/w citric acid.

In a particularly preferred embodiment, the method for dyeing human hair is exemplified in that the third component (K3) contains from about 1.0 to about 8.0% w/w citric acid.

In a particularly preferred embodiment, the method for dyeing human hair is exemplified in that the third component (K3) contains from about 1.5 to about 6.0% w/w citric acid.

In a particularly preferred embodiment, the method for dyeing human hair is exemplified in that the third component (K3) contains from about 2.5 to about 5.5% w/w citric acid.

In a particularly preferred embodiment, the method for dyeing human hair is exemplified in that the third component (K3) contains from about 0.5 to about 15.0% w/w malic acid.

In a particularly preferred embodiment, the method for dyeing human hair is exemplified in that the third component (K3) contains from about 1.0 to about 8.0% w/w malic acid.

In a particularly preferred embodiment, the method for dyeing human hair is exemplified in that the third component (K3) contains from about 1.5 to about 6.0% w/w malic acid.

In a particularly preferred embodiment, the method for dyeing human hair is exemplified in that the third component (K3) contains from about 2.5 to about 5.5% w/w malic acid.

In a particularly preferred embodiment, the method for dyeing human hair is exemplified in that the third component (K3) contains from about 0.5 to about 15.0% w/w tartaric acid.

In a particularly preferred embodiment, the method for dyeing human hair is exemplified in that the third component (K3) contains from about 1.0 to about 8.0% w/w tartaric acid.

In a particularly preferred embodiment, the method for dyeing human hair is exemplified in that the third component (K3) contains from about 1.5 to about 6.0% w/w tartaric acid.

In a particularly preferred embodiment, the method for dyeing human hair is exemplified in that the third component (K3) contains from about 2.5 to about 5.5% w/w tartaric acid.

In a particularly preferred embodiment, the method for dyeing human hair is exemplified in that the third component (K3) contains from about 0.5 to about 15.0% w/w maleic acid.

In a particularly preferred embodiment, the method for dyeing human hair is exemplified in that the third component (K3) contains from about 1.0 to about 8.0% w/w maleic acid.

In a particularly preferred embodiment, the method for dyeing human hair is exemplified in that the third component (K3) contains from about 1.5 to about 6.0% w/w maleic acid.

In a particularly preferred embodiment, the method for dyeing human hair is exemplified in that the third component (K3) contains from about 2.5 to about 5.5% w/w maleic acid.

In a particularly preferred embodiment, the method for dyeing human hair is exemplified in that the third component (K3) contains from about 0.5 to about 10.0% w/w succinic acid.

In a particularly preferred embodiment, the method for dyeing human hair is exemplified in that the third component (K3) contains from about 1.0 to about 8.0% w/w succinic acid.

In a particularly preferred embodiment, the method for dyeing human hair is exemplified in that the third component (K3) contains from about 1.5 to about 6.0% w/w succinic acid.

In a particularly preferred embodiment, the method for dyeing human hair is exemplified in that the third component (K3) contains from about 2.5 to about 5.5% w/w succinic acid.

In a particularly preferred embodiment, the method for dyeing human hair is exemplified in that the third component (K3) contains 0.5 to 10.0% w/w oxalic acid.

In a particularly preferred embodiment, the method for dyeing human hair is exemplified in that the third component (K3) contains from about 1.0 to about 8.0% w/w oxalic acid.

In a particularly preferred embodiment, the method for dyeing human hair is exemplified in that the third component (K3) contains from about 1.5 to about 6.0% w/w oxalic acid.

In a particularly preferred embodiment, the method for dyeing human hair is exemplified in that the third component (K3) contains from about 2.5 to about 5.5% w/w oxalic acid.

In a particularly preferred embodiment, the method for dyeing human hair is exemplified in that the third component (K3) contains from about 0.5 to about 15.0% w/w ascorbic acid.

In a particularly preferred embodiment, the method for dyeing human hair is exemplified in that the third component (K3) contains from about 1.0 to about 8.0% w/w ascorbic acid.

In a particularly preferred embodiment, the method for dyeing human hair is exemplified in that the third component (K3) contains from about 1.5 to about 6.0% w/w ascorbic acid.

In a particularly preferred embodiment, the method for dyeing human hair is exemplified in that the third component (K3) contains from about 2.5 to about 5.5% w/w ascorbic acid.

In a particularly preferred embodiment, the method for dyeing human hair is exemplified in that the third component (K3) contains from about 0.5 to about 15.0% w/w phosphoric acid.

In a particularly preferred embodiment, the method for dyeing human hair is exemplified in that the third component (K3) contains from about 1.0 to about 8.0% w/w phosphoric acid.

In a particularly preferred embodiment, the method for dyeing human hair is exemplified in that the third component (K3) contains from about 1.5 to about 6.0% w/w phosphoric acid.

In a particularly preferred embodiment, the method for dyeing human hair is exemplified in that the third component (K3) contains from about 2.5 to about 5.5% w/w phosphoric acid.

In order to ensure good, homogenous miscibility of the components (K2) or (K3) with the dye component (K1), it is preferable as contemplated herein if at least one of the components (K2) or (K3) contains one of more tensides independently of each other. Under certain circumstances the addition of certain ionic tensides to the component (K2) or (K3) may result in oppositely charged components in the component (K1) interacting when mixing with (K1). This may be desirable, but it may also be undesirable. For reasons of universal usability, it is therefore preferable if component (K2) or—independently thereof—component (K3) contains one or more non-ionic tensides. Non-ionic tensides may also be referred to as non-ionic emulsifiers.

In a particularly preferred embodiment, the method for dyeing human hair is exemplified in that the second component (K2) contains one or more non-ionic tensides.

In a further particularly preferred embodiment, the method for dyeing human hair is exemplified in that the third component (K3) contains one or more non-ionic tensides.

A non-ionic tenside is a tenside that does not carry any electrical charge or charges. In other words, a non-ionic tenside contains no dissociable functional groups and therefore cannot be separated into ions in water. Non-ionic tensides include a non-polar part, preferably a hydrocarbon chain (alkyl chain) with at least 8 carbon atoms, and a polar part. A non-ionic tenside may contain for example a polyethylene glycol unit or a monosaccharide or polysaccharide unit as the polar part.

Fatty alcohols (i.e. C8-C30 alkanols) with a fatty chain and only one hydroxy group are very poorly soluble in water and do not have a sufficiently polar moiety. For this reason, for the purposes of the present disclosure fatty alcohols are treated as fatty components and explicitly not as non-ionic tensides.

The monoesters and diesters of fatty alcohols (i.e. C8-C30 alkanols) and ethylene glycol are also considered to be fatty substances and explicitly not non-ionic tensides.

The monoesters, diesters and triesters of fatty alcohols (i.e. C8-C30 alkanols) and glycerol are also considered to be fatty substances and explicitly not non-ionic tensides.

Suitable non-ionic tensides contain for example a polyol group, a polyalkylene glycol ether group or a combination of polyol- and polyglycol ether group as a hydrophilic group. Such compounds are for example
- adducts of from about 5 to about 50 mol ethylene oxide and/or from about 5 to about 50 mol propylene oxide with linear and branched fatty alcohols having 8 to 30 C atoms, such as lauryl, myristyl, cetyl, or also stearyl, isostearyl and oleyl alcohol, and with fatty acids having 8 to 30 C atoms,
- adducts of from about 5 to about 50 mol ethylene oxide and/or from about 5 to about 50 mol propylene oxide closed at the terminal group thereof by a methyl or C2-C6 alkyl radical with linear and branched fatty alcohols having 8 to 30 C atoms and with fatty acids having 8 to 30 C atoms,
- polyglycerol esters and alkoxylated polyglycerol esters, such as for example poly(3)glycerol diisostearate and poly(2)glycerol polyhydroxy stearate.
- polyol fatty acid esters, such as for example pentaerythrityl distearate,
- higher alkoxylated, preferably ethoxylated, mono-, di- and triglycerides, such as for example glycerol monolaurate+20 ethylene oxide and glycerol monostearate+20 ethylene oxide,
- amine oxides,
- sorbitan fatty acid esters and adducts of ethylene oxide with sorbitan fatty acid esters, such as for example the polysorbates and sorbitan monolaurate+20 mol ethylene oxide (EO),
- sugar fatty acid esters and adducts of ethylene oxide with sugar fatty acid ester,
- adducts of ethylene oxide with fatty acid alkanolamides and fatty amines,
- fatty acid-N-alkylglucamides,
- alkylpolyglycosides corresponding to the general formula RO—(Z)$_x$, wherein R stands for alkyl, Z for sugar and x for the number of sugar units. The alkylpolyglycosides usable as contemplated herein may only contain one specific alkyl radical R. However, these compounds are usually prepared from natural fats and oils or mineral oils. In this case, mixtures corresponding to the starter compounds or corresponding to the respective treatment of said compounds are present as alkyl radicals R.

Ethoxylated fatty alcohols and C8-C22 alkylmono- and oligoglycosides in particularly have proven to be especially preferred non-ionic tensides.

In a particularly preferred embodiment, the method for dyeing human hair is exemplified in that at least one of the components (K2) or (K3) independently of the other contains one or more ethoxylated fatty alcohols with formula (I),

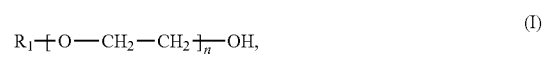

wherein
R1 stands for a saturated or unsaturated, unbranched or branched $C_8$-$C_{30}$ alkyl group, preferably a saturated, unbranched $C_{16}$- or $C_{18}$ alkyl group, and
n stands for an integer from 10 to 120, preferably for an integer from 10 to 80, more preferably for an integer from 10 to 50 and particularly preferably for an integer from 10 to 30.

In a particularly preferred embodiment, the method for dyeing human hair is exemplified in that at least one of the components (K2) or (K3) independently of the other contains one or more alkyl mono- or polyglucosides with formula (II),

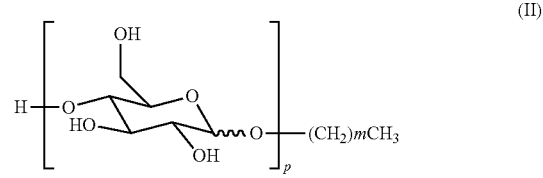

wherein
m stands for an integer from 7 to 21, preferably from 9 to 19, more preferably from 9 to 17 and most particularly preferably from 11 to 15, and
p stands for an integer from 1 to 4, preferably from 1 to 3 and particularly preferably from 1 to 2.

Dyeing methods that are preferred as contemplated herein are the component (K2) contains at least one non-ionic tenside in a total quantity from about 0.2 to about 5% w/w, preferably from about 0.5 to about 2% w/w, and most particularly preferably from about 0.7 to about 1% w/w, relative to the weight thereof in each case.

Further dyeing methods that are preferred as contemplated herein are the component (K3) contains at least one non-ionic tenside in a total quantity from about 0.2 to about 5% w/w, preferably from about 0.5 to about 2% w/w, and most particularly preferably from about 0.7 to about 1% w/w relative to the weight thereof in each case.

With the method as contemplated herein, it is intended that the pH value of the mixture (M2) which is prepared by mixing a partial quantity of the mixture (M1) obtained from (K1) and (K2) with a further quantity of (K2) should be lowered in defined and reproducible manner compared to the pH value of the mixture (M1). As was explained previously, the purpose of this lowering of the pH value is to obtain a homogenous dyeing result.

In this context, it has been found that the homogeneity of the dyeing result may already be significantly reduced if the pH value of the mixture (M2) is at least 0.2 units lower than the pH value of mixture (M1).

In a further, most particularly preferred embodiment, the method for dyeing human hair is exemplified in that
the components (K1) and (K2) contain water and
the pH value of mixture (M2) is at least about 0.2 units lower than the pH value of mixture (M1).

Component (K1) is an aqueous dye preparation which contains at least one oxidation dye precursor and has a pH value in the range from about 8 to about 11, preferably in the range from about 8.5 to about 10.7, particularly preferably in the range from about 9 to about 10.1, measured at 22° C. in each case.

Preferred dyeing methods as contemplated herein are the component (K1) contains at least one oxidation dye precursor of the developer type and at least one oxidation dye precursor of the coupling type.

In a further, most particularly preferred embodiment, the method for dyeing human hair is exemplified in that the first component (K1) contains at least one oxidation dye precursor of the developer type, selected from the group including p-toluylene diamine, 2-(2-Hydroxy-ethyl)-p-phenylene diamine, N,N-Bis-(2-hydroxyethyl)-p-phenylene diamine, 2-Methoxymethyl-p-phenylene diamine, N-(4-Amino-3-methylphenyl)-N-[3-(1H-imidazole-1-yl)propyl]amine, Bis-(2-hydroxy-5-aminophenyl)methane, 4-Aminophenol, 4-Amino-3-methylphenol, 4,5-Diamino-1-(2-hydroxyethyl) pyrazole, 2,4,5,6-Tetraaminopyrimidine, 4-Hydroxy-2,5,6-triaminopyrimidine, 2-Hydroxy-4,5,6-triaminopyrimidine and/or physiologically tolerable salts thereof.

Preferred additional oxidation dye precursors of the developer type are selected from the group including 2-(1, 2-Dihydroxyethyl)-p-phenylene diamine, N,N-Bis-(2-hydroxyethyl)-p-phenylene diamine, 2-Methoxymethyl-p-phenylene diamine, N-(4-Amino-3-methylphenyl)-N-[3-(1H-imidazole-1-yl)propyl]amine, N,N-Bis-(2-hydroxyethyl)-N, N-bis-(4-aminophenyl)-1,3-diamino-propan-2-ol, Bis-(2-hydroxy-5-aminophenyl)methane, 1,3-Bis-(2,5-diaminophenoxy)propan-2-ol, N,N'-Bis-(4-aminophenyl)-1, 4-diazacycloheptane, 1,10-Bis-(2,5-diaminophenyl)-1,4,7, 10-tetraoxadecane, p-Aminophenol, 4-Amino-3-methylphenol, 4-Amino-2-aminomethylphenol, 4-Amino-2-(1,2-dihydroxyethyl)phenol, 4-Amino-2-(diethylaminomethyl)phenol, 2,4,5,6-Tetraaminopyrimidine, 4-Hydroxy-2,5,6-triaminopyrimidine, 2-Hydroxy-4,5,6-triaminopyrimidine, 2,3-Diamino-6,7-dihydro-1H,5H-pyrazolo[1,2-a]pyrazol-1-one and the physiologically tolerable salts thereof.

Coupling components alone do not contribute significantly to the coloring result are part of the direct dyeing process, they always require the presence of developer components. Coupling components within the meaning of the disclosure allow at least one chemical radical of the coupling to be substituted by the oxidized form of the developer component. In this way, covalent bonds are formed between the coupling and the developer component.

Preferably at least one compound from one of the following classes is selected as a suitable coupling component as contemplated herein:
m-Aminophenol and/or derivatives thereof,
m-Dihydroxybenzene and/or derivatives thereof,
m-Diaminobenzene and/or derivatives thereof,
o-Diaminobenzene and/or derivatives thereof,
o-Aminophenol derivatives, such as for example o-Aminophenol,
Naphthalene derivatives with at least one hydroxy group,
Di- or trihydroxybenzene and/or derivatives thereof,
Pyridine derivatives,
Pyrimidine derivatives,
Monohydroxyindole derivatives and/or monoaminoindole derivatives,
Monohydroxyindoline derivatives and/or monoaminoindoline derivatives,
Pyrazolone derivatives, such as for example 1-Phenyl-3-methylpyrazol-5-one,
Morpholine derivatives, such as for example 6-Hydroxybenzomorpholine or 6-Aminobenzomorpholine,
Quinoxaline derivatives, such as for example 6-Methyl-1,2,3,4-tetrahydroquinoxaline.

Mixtures of two or more compounds from one or more of these classes also fall within the scope of the disclosure as part of this embodiment.

Preferred oxidation dye precursors of the coupling type are selected from the group including 3-Aminophenol, 5-Amino-2-methylphenol, 3-Amino-2-chloro-6-methylphenol, 2-Hydroxy-4-aminophenoxy ethanol, 5-Amino-4-chloro-2-methylphenol, 5-(2-Hydroxyethyl)-amino-2-methylphenol, 2,4-Dichloro-3-aminophenol, 2-Aminophenol, 3-Phenylene diamine, 2-(2,4-Diaminophenoxy)ethanol, 1,3-Bis(2,4-diaminophenoxy)propane, 1-Methoxy-2-amino-4-(2-hydroxyethylamino)benzene, 1,3-Bis(2,4-diaminophenyl)propane, 2,6-Bis(2'-hydroxy-ethylamino)-1-methylbenzene, 2-({3-[(2-Hydroxyethyl)amino]-4-methoxy-5-methylphenyl}-amino)ethanol, 2-({3-[(2-Hydroxyethyl)amino]-2-methoxy-5-methylphenyl}amino) ethanol, 2-({3-[(2-Hydroxyethyl)amino]-4,5-dimethylphenyl}amino)ethanol, 2-[3-Morpholin-4-ylphenyl)amino]ethanol, 3-Amino-4-(2-methoxyethoxy)-5-methylphenylamine, 1-Amino-3-bis-(2-hydroxyethyl) aminobenzene, resorcinol, 2-Methylresorcinol, 4-Chlororesorcinol, 1,2,4-Trihydroxybenzol, 2-Amino-3-hydroxypyridine, 3-Amino-2-methylamino-6-methoxypyridine, 2,6-Dihydroxy-3,4-dimethylpyridine, 3,5-Diamino-2,6-dimethoxypyridine, 1-Phenyl-3-methylpyrazol-5-one, 1-Naphthol, 1,5-Dihydroxynaphthalene, 2,7-Dihydroxynaphthalene, 1,7-Dihydroxynaphthalene, 1,8-Dihydroxynaphthalene, 4-Hydroxyindole, 6-Hydroxyindole, 7-Hydroxyindole, 4-Hydroxyindoline, 6-Hydroxyindoline and/or 7-Hydroxyindoline and physiologically tolerably salts thereof.

In addition, the component (K1) may further contain one or more additional direct coloring agents.

The pH value of the component (K1) is alkaline and is in the pH value range from about 8 to about 11, preferably in the range from about 8.5 to about 10.7, particularly preferably in the range from about 9 to about 10.1, measured in each case at 22° C. The alkalizing agents that are usable to set the preferred pH values as contemplated herein are selected from the group including ammonia, alkanolamines, basic amino acids, and inorganic alkalizing agents such as alkaline (earth) metal hydroxides, alkaline (earth) metal metasilicates, alkaline (earth) alkali metal phosphates and alkaline (earth) alkali metal hydrogen phosphates. Preferred inorganic alkalizing agents are sodium hydroxide, potassium hydroxide, sodium silicate and sodium metasilicate. Preferred organic alkalizing agents as contemplated herein are selected from monoethanolamine, 2-Amino-2-methylpropanol and triethanolamine. The basic amino acid which are usable preferably as alkalizing agent as contemplated herein are preferably selected from the group including arginine, lysine, ornithine and histidine, particularly preferably arginine. It was found in the course of the research for the present disclosure that the method as contemplated herein is particularly suitable for dye components (K1) that contain ammonium hydroxide as the alkalizing agent, particularly for those dyes components (K1) that contain ammonium hydroxide as the primary alkalizing agent. For the purposes of the disclosure, such a primary alkalizing agent is understood to be an alkalizing agent which constitutes at least about 55% w/w, preferably at least about 70% w/w, particularly preferably at least about 80% w/w, most especially preferably at least about 90% w/w of the total quantity of all alkalizing agents relative to the weight of the dye component (K1).

It was further found in the course of the research for the present disclosure that the method as contemplated herein is particularly suitable for dye components (K1) that contain at least one lipid in a total quantity from about 0.5 to about 70% w/w, preferably from about 5 to about 50% w/w, particularly preferably from about 10 to about 30% w/w, most especially preferably from about 15 to about 25% w/w, relative in each case to the weight of the component (K1). In this context, the lipids suitable for (K1) are selected from the same substance classes as the lipids that were selected as disclosed previously as suitable for (K2) and (K3), that is to say selected from the group of C12-C30 fatty alcohols, C12-C30 fatty acid triglycerides, esters of linear or branched, saturated or unsaturated fatty alcohols having 2-30 carbon atoms with linear or branched, saturated or unsaturated fatty acids having 2-30 carbon atoms, which may or may not be hydroxylated, C12-C30 fatty acid monoglycerides, C12-C30 fatty acid diglycerides and/or hydrocarbons.

It was further found in the course of the research for the present disclosure that the method as contemplated herein is particularly suitable for dye components (K1) that contain at least one cationic polymer, preferably in a total quantity from about 0.01 to about 5% w/w, more preferably from about 0.05 to about 2% w/w, particularly preferably from about 0.1 to about 1.5% w/w, most especially preferably from about 0.2 to about 1% w/w, relative in each case to the weight of the component (K1).

Cationic polymer preferred as contemplated herein are selected from cationic polymers that are formed from monomers with quaternary ammonium groups having general formula (IIa),

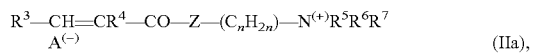
(IIa), in which $R^3$ and $R^4$ are independent of one another and stand for hydrogen or a methyl group, $R^5$, $R^6$ and $R^7$ are independent of one another and stand for an alkyl group with 1 to 4 carbon atoms, Z stands for a NH group or an oxygen atom, n stands for an integer from 2 to 4, and $A^{(-)}$ represents the anion of an inorganic or organic acid, preferably selected from cationic polymers that are formed from acrylamidopropyltrimethyl ammonium chloride, particularly preferably selected from amphoteric polymers with cationic net charge, which are formed by polymerization from a) cationic monomers with quaternary ammonium groups having general formula (IIa),

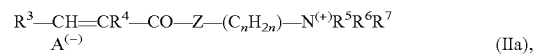
(IIa), in which $R^3$ and $R^4$ are independent of one another and stand for hydrogen or a methyl group, $R^5$, $R^6$ and $R^7$ are independent of one another and stand for an alkyl group with 1 to 4 carbon atoms, Z stands for a NH group or an oxygen atom, n stands for an integer from 2 to 4, and $A^{(-)}$ represents the anion of an inorganic or organic acid, and b) at least one unsaturated carboxylic acid selected from acrylic acid, methacrylic acid and crotonic acid and mixtures of these acid, wherein the at least one unsaturated carboxylic acid may be present in the form of its salts, wherein the cationic monomers are present in the polymer in a molar excess compared with the anionic monomers;

most especially preferably selected from amphoteric polymers with cationic net charge which contain the at least one monomer type having general formula (IIa) and the at least one monomeric unsaturated carboxylic acid type selected from acrylic acid, methacrylic acid and crotonic acid and mixtures thereof, in a molar ratio relative to each other from about 60:40 to about 95:5, preferably from about 75:25 to about 90:10, most particularly especially preferably selected from amphoteric copolymers with cationic net charge which include acrylamidopropyltrimethyl ammonium chloride and acrylic acid in a molar ratio relative to each other from about 60:40 to about 95:5, preferably from about 75:25 to about 90:10;

2-[2-Hydroxy-3-(trimethylammonio)propoxy]ethylcellulose ether chloride, which is available for example under INCI designation Polyquaternium-10, Terpolymers from acrylic acid, diallyldimethyl ammonium chloride and acrylamide, as are available for example under INCI designation Polyquaternium-39, Homopolymers of N,N,N-Trimethyl-2-[(methyl-1-oxo-2-propenyl)oxy]ethanaminium chloride, as are available for example under INCI designation Polyquaternium-37, Copolymers from diallyldimethyl ammonium chloride and acrylic acid, as are available for example under INCI designation Polyquaternium-22, Hydroxyethylcellulose dimethyldiallyl ammonium chloride copolymer as are available for example under INCI designation Polyquaternium-4, Copolymers from acrylamide and beta-Methacrylyloxyethyltrimethyl ammonium methosulfate, as are available for example under INCI designation Polyquaternium-5, Homopolymers of N,N-Dimethyl-N-2-Propenyl-2-Propen-1-aminiumchlorid as are available for example under INCI designation Polyquaternium-6, Copolymers from diallyldimethyl ammonium chloride and acrylamide, as are available for example under INCI designation Polyquaternium-7, Copolymers from vinylpyrrolidone and dimethylaminoethylmethacrylate diethyl sulfate, as are available for example under INCI designation Polyquaternium-11, Quaternized celluloses selected from Polyquaternium-10, Polyquaternium-24, Polyquaternium-67 and Polyquaternium-72, The polymers with quaternary nitrogen atoms in the primary polymer chain known under the designations Polyquaternium-2, Polyquaternium-17, Polyquaternium-18 and Polyquaternium-27, and mixtures of the aforementioned polymers.

Most especially preferred cationic polymers as contemplated herein are selected from Polyquaternium-2,2-[2-Hydroxy-3-(trimethylammonio)propoxy]ethyl cellulose ether chloride, amphoteric copolymers with cationic net charge including acrylamidopropyltrimethyl ammonium chloride and acrylic acid in a molar ratio to each other from about 60:40 to about 95:5, preferably from about 75:25 to about 90:10, and terpolymers from acrylic acid, diallyldimethyl ammonium chloride and acrylamide, and mixtures of said polymers.

It was further found in the course of the research for the present disclosure that the method as contemplated herein is particularly suitable for dye components (K1) which contain at least one anionic surfactant selected from alkyl sulfates and alkylether sulfates, each having 10 to 20 C atoms in the alkyl group and zero to 16, preferably 2 to 3 glycolether groups in the molecule, preferably in a total quantity from about 0.01 to about 5% w/w, preferably from about 0.1 to about 3% w/w, particularly preferably about 0.5 to about 2% w/w, most especially preferably from about 0.7 to about 1.3% w/w relative in each case to the weight of the component (K1).

The at least one alkyl sulfate having 10 to 20 C atoms in the alkyl group and zero glycolether groups in the molecule is preferably selected from lauryl sulfate, myristyl sulfate, cetyl sulfate, stearyl sulfate and arachidyl sulfate and from mixtures of these alkyl sulfates, particularly preferably from cetyl sulfate, stearyl sulfate, arachidyl sulfate and cetyl sulfate/stearyl sulfate mixtures. The alkyl sulfate are monovalent negatively charged and are present in the form of a salt, preferably as alkaline, alkaline earth, ammonium, alkylammonium, alkanolamine or glucammonium salt, particularly preferably as sodium, potassium, alkanolamine, particularly monoethanolamine, trialkylammonium, triethanolamine, 2-Amino-1-butanol-, 2-Amino-2-methyl-1-propanol-, 2-Amino-2-methyl-1,3-propanediol, 2-Amino-2-ethyl-1,3-propansdiol and/or Tris-(hydroxymethyl)aminomethane salt.

As contemplated herein the at least one alkyl sulfate having 10 to 20 C atoms in the alkyl group and zero glycolether groups in the molecule is particularly preferably present in the form of the sodium, potassium, or magnesium salt. Most especially preferably, the at least one alkyl sulfate having 10 to 20 C atoms in the alkyl group and zero glycolether groups in the molecule is selected from sodium lauryl sulfate, sodium myristyl sulfate, sodium cetyl sulfate, sodium stearyl sulfate, sodium arachidyl sulfate, potassium lauryl sulfate, potassium myristyl sulfate, potassium cetyl sulfate, potassium stearyl sulfate, potassium arachidyl sulfate and mixtures of these alkyl sulfates. Also most especially preferably, the at least one alkyl sulfate having 10 to 20 C atoms in the alkyl group and zero glycolether groups in the molecule is selected from sodium cetyl sulfate, sodium stearyl sulfate, potassium cetyl sulfate, potassium stearyl sulfate and mixtures of these alkyl sulfates.

The at least one alkylether sulfate having from about 10 to about 20 C atoms in the alkyl group and from about 1 to about 16 glycolether groups in the molecule is preferably selected from laureth sulfate, myristeth sulfate, ceteth sulfate, steareth sulfate and arachideth sulfate, and from mixtures of these alkylether sulfates. Particularly preferably, the at least one alkylether sulfate having 10 to 20 C atoms in the alkyl group and 1 to 16 glycolether groups in the molecule is selected from ceteth sulfate, steareth sulfate, arachideth sulfate and ceteth-sulfate/steareth sulfate mixtures, wherein the alkylether sulfates particularly preferably have from about 2 to about 3 glycolether groups in the molecule. The alkylether sulfates in this case are monovalent negatively charged and are present in the form of a salt, preferably as alkaline, alkaline earth, ammonium, alkylammonium, alkanolamine or glucammonium salt, particularly preferably as sodium, potassium, alkanolamine, particularly monoethanolamine, trialkylammonium, triethanolamine, 2-Amino-1-butanol, 2-Amino-2-methyl-1-propanol, 2-Amino-2-methyl-1,3-propanediol, 2-Amino-2-ethyl-1,3-propanediol and/or tris-(hydroxy-methyl)aminomethane salt.

Particularly preferably as contemplated herein, the at least one alkylether sulfate having 10 to 20 C atoms in the alkyl group and from about 1 to about 16, preferably from about 2 to about 3 glycolether groups in the molecule is in the form of the sodium, potassium, or magnesium salt. Most especially preferably, the at least one alkylether sulfate having 10 to 20 C atoms in the alkyl group and from about 1 to about 16, preferably from about 2 to about 3 glycolether groups in the molecule is selected from sodium laureth sulfate, sodium myristeth sulfate, sodium ceteth sulfate, sodium steareth sulfate, sodium arachideth sulfate, potassium laureth sulfate, potassium myristeth sulfate, potassium ceteth sulfate, potassium steareth sulfate, potassium arachideth sulfate and mixtures of these alkylether sulfates. Also most especially preferably, the at least one alkylether sulfate having 10 to 20 C atoms in the alkyl group and from about 1 to about 16, preferably from about 2 to about 3 glycolether groups in the molecule is selected from sodium laureth(2)sulfate, sodium laureth(3)sulfate, potassium laureth(2)sulfate and potassium laureth(3)sulfate and from mixtures of these alkylether sulfates.

A most especially preferred dyeing method as contemplated herein is exemplified in that the first component (K1) contains the following ingredients:

Ammonium hydroxide as primary alkalizing agent, that is to say ammonium hydroxide in a quantity of at least about 55% w/w, preferably at least about 70% w/w, particularly preferably at least about 80% w/w, most especially preferably at least about 90% w/w of the total quantity of all alkalizing agents, in the component (K1), and at least one lipid in a total quantity from about 0.5 to about 70% w/w, preferably from about 5 to about 50% w/w, particularly preferably from about 10 to about 30% w/w, most especially preferably from about 15 to about 25% w/w relative in each case to the weight of the component (K1), and at least one cationic polymer, preferably in a total quantity from about 0.01 to about 5% w/w, more preferably from about 0.05 to about 2% w/w, particularly preferably from about 0.1 to about 1.5% w/w, most especially preferably from about 0.2 to about 1% w/w relative in each case to the weight of the component (K1), particularly preferably selected from Polyquaternium-2,2-[2-Hydroxy-3-(trimethylammonio)propoxy]ethylcellulose ether chloride, amphoteric copolymers with cationic net charge which include acrylamidopropyltrimethylammonium chloride and acrylic acid in a molar ratio to each other from about 60:40 to about 95:5, preferably from about 75:25 to about 90:10, and terpolymers from acrylic acid, diallyl dimethylammonium chloride and acrylamide, as well as mixtures of said polymers; and at least one anionic surfactant selected from alkyl sulfates and alkylether sulfates, each having 10 to 20 C atoms int the alkyl group and from about zero to about 16, preferably from about 2 to about 3 glycolether groups in the molecule, preferably in a total quantity from about 0.01 to about 5% w/w, more preferably from about 0.1 to about 3% w/w, particularly preferably from about 0.5 to about 2% w/w, most especially preferably from about 0.7 to about 1.3% w/w relative in each case to the weight of the component (K1).

The person skilled in the art will select the quantity of oxidizing agents according to the desired lightening strength. If it is intended to produce a very dark shade, the person skilled in the art will reduce the quantity of hydrogen peroxide introduced accordingly. On the other hand, if a lighter fashionable tint is to be applied to dark hair, the hair must also be lightened considerably at the same time. In this case, a correspondingly large quantity of hydrogen peroxide for use must be selected.

In a further most particularly preferred embodiment, the method for dyeing human hair is exemplified in that the second component (K2) contains from about 1.5 to about 18% w/w, preferably from about 2.5 to about 12% w/w, more preferably from about 3 to about 9% w/w and most especially preferably from about 5.5 to about 6.5% w/w hydrogen peroxide (calculated as 100% hydrogen peroxide) relative to the weight of the component (K2).

In a further most particularly preferred embodiment, the method for dyeing human hair is exemplified in that the third component (K3) contains from about 1.5 to about 18% w/w, preferably from about 2.5 to about 12% w/w, more preferably from about 3 to about 9% w/w and most especially preferably from about 5.5 to about 6.5% w/w hydrogen peroxide (calculated as 100% hydrogen peroxide) relative to the weight of the component (K3)

In a further most particularly preferred embodiment, the method for dyeing human hair is exemplified in that the second component (K2) and the third component (K3) independently of each other and relative to the weight thereof in each case contain from about 1.5 to about 18% w/w, preferably from about 2.5 to about 12% w/w, more preferably from about 3 to about 9% w/w and most especially preferably from about 5.5 to about 6.5% w/w hydrogen peroxide.

The components (K1) and (K2) in the method as contemplated herein are preferably mixed with each other in certain weight ratios. The first component (K1) and the second component (K2) are preferably mixed with each other in a weight ratio from about 3:1 to about 1:3, preferably from about 2:1 to about 2:1, most especially preferably about 1:1.

The Components (K1) and (K3) in the method as contemplated herein are preferably mixed with each other in certain weight ratios. The first component (K1) and the third component (K3) are preferably mixed with each other in a weight ratio from about 3:1 to about 1:3, preferably from about 2:1 to about 2:1, most especially preferably about 1:1.

In principle, the weight ratios (K1):(K2) and (K1):(K3) are independent of each other. However, for reasons of user friendliness, it may be preferable if the weight ratios (K1):(K2) and (K1):(K3) are identical.

After application to the hair, in step E) the mixtures (M1) and (M2) are left on the hair to take effect for a period lasting from about 30 seconds to about 60 minutes, preferably from about 20 to about 45 minutes. In this step, it is possible as contemplated herein to leave the mixture (M2) on all regions of the hair for a certain period, at about room temperature and/or at from about 30 to about 60° C., preferably at from about 32 to about 50° C. However, in a further embodiment it is also possible to select different exposure periods for certain regions of the hair shaft, so that for example the exposure period in the middle portion of the hair shaft is made longer than the exposure period in the area of the tips by rinsing the mixture (M2) off the hair tips first, and leaving it on the middle region of the shaft region for longer.

In a further, most particularly preferred embodiment, the method for dyeing human hair is:

E1) the mixture (M2) is applied to the hair in the region of the middle of the hair shaft WITHOUT the hair tips for a period from about 30 seconds to about 60 minutes, preferably from about 20 to about 45 minutes, and E2) the mixture (M2) is applied to the hair in the region that was not treated previously in step E1), that is to say particularly the hair tips, for a period from about 30 seconds to about 60 minutes, preferably from about 20 to about 45 minutes wherein the exposure periods of steps E1) and E2) differ by at least about 5 minutes, preferably at least about 10 minutes.

Examples

The following formulations were prepared—unless otherwise indicated, all values are expressed as percentage by weight.

1. Dye Preparation (First Component (K1))

|  | % w/w |
|---|---|
| Polyacrylic acid-Ammonium salt (active substance) | 0.075 |
| Decyl oleate | 2.1 |
| Sodium cetearyl sulfate | 1.3 |
| Cetearyl alcohol | 14.9 |
| Glyceryl stearate | 5.4 |
| Linoleamidopropyl PG-dimonium chloride phosphate | 0.05 |
| EDTA | 0.8 |
| Monoethanolamine | 0.4 |
| Ammonia (25% w/w aqueous solution) | 8.0 |
| Ascorbic acid | 0.1 |
| Sodium dithionite | 0.1 |
| L-serine | 0.3 |
| Polyquaternium-2 | 0.1 |
| p-Toluylene diamine sulfate | 0.8 |
| Resorcinol | 0.2 |
| m-Aminophenol | 0.04 |
| 4-Chlororesorcinol | 0.2 |
| 2-Amino-4-[(2-hydroxyethyl)amino]-anisole | 0.02 |
| Water | ad 100 |

2. Oxidizing Agent Composition (Component (K2))

|  | % w/w |
|---|---|
| Sodium benzoate | 0.04 |
| Dipicolinic acid | 0.1 |
| Disodium pyrophosphate | 0.1 |
| Potassium hydroxide | 0.1 |
| 1,2-Propanediol | 1.0 |
| Etidronic acid (1-Hydroxyethan-1,1-diphosphonic acid) | 0.15 |
| Paraffinum liquidum | 0.3 |

-continued

| | % w/w |
|---|---|
| Steartrimonium chloride | 0.31 |
| Cetearyl alcohol | 3.4 |
| Ceteareth-20 | 1.0 |
| Isopropyl alcohol | 0.07 |
| Hydrogen peroxide | 6.1 |
| Water | ad 100 |

Composition K2 has a pH value of 3.28, measured at 22° C.

3. Oxidizing Agent Composition (Component (K3-1))

| | % w/w |
|---|---|
| Sodium benzoate | 0.04 |
| Dipicolinic acid | 0.1 |
| Disodium pyrophosphate | 0.1 |
| Potassium hydroxide | 0.1 |
| 1,2-Propanediol | 1.0 |
| Etidronic acid (1-Hydroxyethan-1,1-diphosphonic acid) | 0.15 |
| Paraffinum liquidum | 0.3 |
| Steartrimonium chloride | 0.31 |
| Cetearyl alcohol | 3.4 |
| Ceteareth-20 | 1.0 |
| Isopropyl alcohol | 0.07 |
| Phosphoric acid, 85% w/w | 1.0 |
| Hydrogen peroxide | 6.1 |
| Water | ad 100 |

Composition K3-1 has a pH value of 1.14, measured at 22° C.

4. Oxidizing Agent Composition (Component (K3-2))

| | % w/w |
|---|---|
| Sodium benzoate | 0.04 |
| Dipicolinic acid | 0.1 |
| Disodium pyrophosphate | 0.1 |
| Potassium hydroxide | 0.1 |
| 1,2-Propanediol | 1.0 |
| Etidronic acid (1-Hydroxyethan-1,1-diphosphonic acid) | 0.15 |
| Paraffinum liquidum | 0.3 |
| Steartrimonium chloride | 0.31 |
| Cetearyl alcohol | 3.4 |
| Ceteareth-20 | 1.0 |
| Isopropyl alcohol | 0.07 |
| Lactic acid or Tartaric acid or Malic acid | @ pH 1.4 |
| Hydrogen peroxide | 6.1 |
| Water | ad 100 |

5. Oxidizing Agent Composition (Component (K3-3))

| | % w/w |
|---|---|
| Sodium cetearyl sulfate | 0.34 |
| Cetearyl alcohol | 3.5 |
| PEG-40 castor oil | 0.7 |
| Potassium hydroxide | 0.12 |
| Sodium benzoate | 0.04 |
| Disodium pyrophosphate | 0.1 |
| Dipicolinic acid | 0.1 |
| Etidronic acid (1-Hydroxyethan-1,1-diphosphonic acid) | 0.19 |
| Paraffinum liquidum | 17.0 |
| Phosphoric acid or lactic acid or tartaric acid or malic acid | @ pH 1.4 |
| Hydrogen peroxide | 6.1 |
| Water | ad 100 |

3. Application

First the dye preparation (K1) was mixed with the oxidizing agent composition (K2) in a weight ratio of 1:1. As a result of this mixing operation, the mixture (M1) was obtained.

This mixture was applied to the hair at the hair anchor point.

Then the dye preparation (K1) was mixed with one of the oxidizing agent compositions (K3-1), (K3-2) or (K3-3) in a weight ratio of 1:1. As a result, the mixture (M2) was obtained.

The following pH values were obtained for the 1:1 mixtures (22° C.)

| | K1 | (K1) + (K2) = (M1) | (K1) + (K3-1) = (M2-1) | (K1) + (K3-2) = (M2-2) | (K1) + (K3-3) = (M2-3) |
|---|---|---|---|---|---|
| pH value | 10.44 | 10.05 | 9.79 | 9.77 | 9.78 |

The invention claimed is:

1. A method for dyeing human hair, comprising, in the sequence indicated, the steps of:
    mixing a first portion of a first component (K1) with a second component (K2) to obtain a first mixture (M1),
    applying the first mixture (M1) to selected regions of the hair including a hair anchor point,
    mixing a second portion of the first component (K1) with a third component (K3) to obtain a second mixture (M2),
    applying the second mixture (M2) to selected regions of the hair, which were not treated with the first mixture (M1), including to a hair shaft and/or hair tips,
    allowing the first and second mixtures (M1) and (M2) to take effect on the hair for a period from about 30 seconds to about 60 minutes at about room temperature or at from about 30 to about 60° C.,
    rinsing the first and second mixtures (M1) and (M2) out of the hair,
    wherein:
    the first component (K1) is an aqueous dye preparation which comprises at least one oxidation dye precursor and has a pH value from about 8 to about 11, measured at 22° C.,
    the second component (K2) is an aqueous hydrogen peroxide preparation which comprises no oxidation dye precursors and has a pH value from about 3 to about 6.9, measured at 22° C., and
    the third component (K3) is an aqueous hydrogen peroxide preparation which comprises no oxidation dye precursors and has a pH value from about 1.0 to about 2.8, measured at 22° C., and
    the pH value of the first mixture (M1) is at least about 0.2 units lower than the pH value of the component (K1) and
    the pH value of the second mixture (M2) is at least about 0.2 units lower than the pH value of the first component (M1).

2. The method according to claim 1, wherein the second component (K2) comprises one or more lipids in a total quantity from about 0.1 to about 70% w/w, relative to the weight thereof.

3. The method according to claim 1, wherein the third component (K3) comprises one or more lipids in a total quantity from about 0.1 to about 70% w/w, relative to the weight thereof.

4. The method according to claim 1, wherein the third component (K3) comprises at least one acid selected from the group of lactic acid, citric acid, malic acid, tartaric acid, maleic acid, succinic acid, oxalic acid, ascorbic acid, sulfuric acid, hydrochloric acid and/or phosphoric acid.

5. The method according to claim 1, wherein the third component (K3) comprises one or more acids in a total quantity from about 0.5 to about 15.0% w/w, relative to the weight of third component (K3).

6. The method according to claim 1, wherein the third component (K3) comprises at least one acid selected from the group of lactic acid, citric acid, malic acid, tartaric acid, maleic acid, succinic acid, oxalic acid, ascorbic acid, sulfuric acid, hydrochloric acid and/or phosphoric acid in a total quantity from about 0.5 to about 15.0% w/w, relative to the weight of third component (K3).

7. The method according to claim 1, wherein the second component (K2) comprises one or more non-ionic tensides.

8. The method according to claim 1, wherein the third component (K3) comprises one or more non-ionic tensides.

9. The method according to claim 1, wherein the first component (K1) comprises at least one oxidation dye precursor selected from the group of p-toluylene diamine, 2-(2-hydroxyethyl)-p-phenylene diamine, N,N-bis-(2-hydroxyethyl)-p-phenylene diamine, 2-methoxymethyl-p-phenylene diamine, N-(4-amino-3-methylphenyl)-N-[3-(1H-imidazole-1-yl)propyl]amine, bis-(2-hydroxy-5-aminophenyl)methane, 4-aminophenol, 4-amino-3-methylphenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine and/or physiologically tolerable salts thereof.

10. The method according to claim 1, wherein the second component (K2) and the third component (K3) independently comprise from about 1.5 to about 18% w/w hydrogen peroxide relative.

11. The method according to claim 1, wherein:
the first component (K1) and the second component (K2) are mixed together in a weight ratio from about 3:1 to about 1:3, and/or
the first component (K1) and the third component (K3) are mixed together in a weight ratio from about 3:1 to about 1:3.

12. The method according to claim 1, wherein the first component (K1) comprises:
ammonium hydroxide as primary alkalizing agent in a quantity of at least about 55% w/w, of the total quantity of all alkalizing agents, in the component (K1), and/or
at least one lipid in a total quantity from about 0.5 to about 70% w/w, relative to the weight of the component (K1), and/or
at least one cationic polymer, in a total quantity from about 0.01 to about 5% w/w, relative to the weight of the component (K1); and/or
at least one anionic surfactant selected from alkyl sulfates and alkylether sulfates, each having 10 to 20 C atoms in the alkyl group and zero to 16 glycolether groups in the molecule, in a total quantity from about 0.01 to about 5% w/w relative to the weight of the first component (K1).

13. The method according to claim 1, wherein the first component (K1) comprises:
Ammonium hydroxide as primary alkalizing agent in a quantity of at least about 55% w/w, of the total quantity of all alkalizing agents, in the first component (K1), and
at least one lipid in a total quantity from about 0.5 to about 70% w/w relative to the weight of the first component (K1), and
at least one cationic polymer in a total quantity from about 0.01 to about 5 w/w relative to the weight of the first component (K1) wherein the at least one cationic polymer is selected from Polyquaternium-2,2-[2-Hydroxy-3-(trimethylammonio)propoxy]ethylcellulose ether chloride, amphoteric copolymers with cationic net charge which consist of acrylamidopropyltrimethylammonium chloride and acrylic acid in a molar ratio to each other from about 60:40 to about 95:5, and terpolymers from acrylic acid, diallyl dimethylammonium chloride and acrylamide, and mixtures thereof; and
at least one anionic surfactant selected from alkyl sulfates and alkylether sulfates, each having from 10 to 20 C atoms in the alkyl group and from zero to 16 glycolether groups in the molecule, in a total quantity from about 0.01 to about 5% w/w relative to the weight of the first component (K1).

14. The method according to claim 1, wherein the second component (K2) comprises one or more lipids in a total quantity from about 2 to about 50 w/w relative to the weight thereof.

15. The method according to claim 1, wherein the second component (K2) comprises one or more lipids in a total quantity from about 3.5 to about 21% w/w relative to the weight thereof.

16. The method according to claim 1, wherein the second component (K2) comprises one or more lipids in a total quantity from about 8 to about 15% relative to the weight thereof.

17. The method according to claim 1, wherein the third component (K3) comprises one or more lipids in a total quantity from about 2 to about 50 w/w relative to the weight thereof.

18. The method according to claim 1, wherein the third component (K3) comprises one or more lipids in a total quantity from about 3.5 to about 21% w/w relative to the weight thereof.

19. The method according to claim 1, wherein the third component (K3) comprises one or more lipids in a total quantity from about 8 to about 15 w/w relative to the weight thereof.

* * * * *